US012667435B2

(12) United States Patent
Yang

(10) Patent No.: US 12,667,435 B2
(45) Date of Patent: Jun. 30, 2026

(54) CONNECTING STRUCTURES AND SURGICAL ROBOT

(71) Applicant: CORNERSTONE TECHNOLOGY (SHENZHEN) LIMITED, Shenzhen (CN)

(72) Inventor: Qiusheng Yang, Shenzhen (CN)

(73) Assignee: CORNERSTONE TECHNOLOGY (SHENZHEN) LIMITED, Shenzhen (CN)

( * ) Notice: Subject to any disclaimer, the term of this patent is extended or adjusted under 35 U.S.C. 154(b) by 242 days.

(21) Appl. No.: 18/409,672

(22) Filed: Jan. 10, 2024

(65) Prior Publication Data

US 2024/0148450 A1 May 9, 2024

Related U.S. Application Data

(63) Continuation of application No. PCT/CN2022/100504, filed on Jun. 22, 2022.

(30) Foreign Application Priority Data

Jul. 14, 2021 (CN) .......................... 202110795324.9
Jul. 14, 2021 (CN) .......................... 202110795336.1

(51) Int. Cl.
*A61B 34/30* (2016.01)
*A61B 17/00* (2006.01)

(52) U.S. Cl.
CPC .............. *A61B 34/30* (2016.02); *A61B 17/00* (2013.01); *A61B 2017/00486* (2013.01)

(58) Field of Classification Search
CPC .......... A61B 17/00; A61B 2017/00477; A61B 2017/00486; A61B 2090/034;

(Continued)

(56) References Cited

U.S. PATENT DOCUMENTS

2014/0165770 A1    6/2014    Abri et al.
2015/0202009 A1*   7/2015    Nussbaumer .......... A61B 46/10
                                                        128/856

(Continued)

FOREIGN PATENT DOCUMENTS

CN          106102631 A    11/2016
CN          106132342 A    11/2016

(Continued)

OTHER PUBLICATIONS

Cornerstone Technology (Shenzhen) Limited, Extended European Search Report, EP 22841146.8, Aug. 22, 2024, 20 pgs.

(Continued)

*Primary Examiner* — Scott Luan
(74) *Attorney, Agent, or Firm* — ScienBiziP, P.C.

(57) ABSTRACT

The present disclosure discloses a structure for connecting a sterile adapter to a surgical instrument and a surgical robot. A plurality of first engaging members are provided on the sterile adapter and are configured to connect the sterile adapter to the surgical instrument. At least one fixing assembly is provided at a base of the surgical instrument and is configured to fix the base to the sterile adapter, each fixing assembly includes a moveable component provided with a plurality of second engaging members operably engaged with first engaging members. The moveable component is moveable between a locked position where the plurality of second engaging members are engaged with the plurality of first engaging members and an unlocked position where the plurality of second engaging members are detached from the plurality of first engaging members, and the moveable component has a movement path parallel to a surface of the sterile adapter.

20 Claims, 12 Drawing Sheets

(58) Field of Classification Search
CPC . A61B 2090/0813; A61B 34/30; A61B 34/70;
A61B 46/10
See application file for complete search history.

(56) References Cited

U.S. PATENT DOCUMENTS

| | | | |
|---|---|---|---|
| 2015/0257842 A1 | 9/2015 | Dachs | |
| 2016/0367328 A1 | 12/2016 | Dachs et al. | |
| 2018/0168753 A1 | 6/2018 | Scheib et al. | |
| 2018/0221095 A1 | 8/2018 | Bailey et al. | |
| 2018/0325616 A1* | 11/2018 | Kapadia | A61B 34/30 |
| 2020/0069381 A1 | 3/2020 | Betsugi et al. | |

FOREIGN PATENT DOCUMENTS

| | | | |
|---|---|---|---|
| CN | 108472029 A | | 8/2018 |
| CN | 210019646 U | | 2/2020 |
| CN | 112022244 A | | 12/2020 |
| CN | 112426184 | * | 3/2021 |
| CN | 112426184 A | | 3/2021 |
| CN | 113288431 A | | 8/2021 |
| CN | 113349934 A | | 9/2021 |
| CN | 113349936 A | | 9/2021 |
| CN | 113425415 A | | 9/2021 |
| CN | 113693727 A | | 11/2021 |
| CN | 217853296 U | | 11/2022 |
| CN | 218474636 U | | 2/2023 |
| EP | 3616641 A1 | | 3/2020 |
| EP | 3797726 A1 | | 3/2021 |
| WO | 2011037394 A2 | | 3/2011 |

OTHER PUBLICATIONS

Cornerstone Technology (Shenzhen) Limited, International Search Report with English translation, PCT/CN2022/100504, Sep. 13, 2022, 8 pgs.
Cornerstone Technology (Shenzhen) Limited, Extended European Search Report, EP 24153782.8, May 10, 2024, 7 pgs.
Cornerstone Technology (Shenzhen) Limited, U.S. Appl. No. 18/409,665, filed Nov. 26, 2025, 30 pgs.

* cited by examiner

100

100

150

100

CONNECTING STRUCTURES AND SURGICAL ROBOT

CROSS REFERENCE TO RELATED APPLICATIONS

The present application is a continuation of PCT application No. PCT/CN2022/100504, entitled "CONNECTING STRUCTURES AND SURGICAL ROBOT," filed on Jun. 22, 2022, which claims priority to Chinese patent application No. 202110795336.1, filed on Jul. 14, 2021, and Chinese patent application No. 202110795324.9, filed on Jul. 14, 2021, each of which is incorporated by reference herein in its entirety.

TECHNICAL FIELD

The present disclosure relates to the field of medical instrument technology, and in particular to a structure for connecting an instrument drive to a sterile adapter, a structure for connecting a sterile adapter to a surgical instrument, and a surgical robot.

BACKGROUND

A surgical robot can assist doctors in precise positioning during surgery, and has advantages of reducing wounds of a patient and shortening postoperative recovery time. Moreover, the surgical robot has a stable operating platform that can reduce or prevent trembling of doctors. Thus, surgical robots are widely used in clinical surgical operations.

A surgical robot at the patient end performs surgical operations through a surgical instrument equipped with at least one end effector. In order to meet the usage requirements of various surgical instruments during surgery, surgical instruments and instrument drives are usually designed to be detachable to facilitate replacement of various surgical instruments during surgery. Moreover, surgical instruments are usually designed to be capable of independent sterilization.

The instrument drive end is usually designed to be not capable of sterilization. To ensure sterility during surgery, a sterile adapter is added between the instrument drive and the surgical instruments to isolate the non-sterile instrument drive end and the sterile surgical instrument end during surgery.

At present, a sterile adapter and an instrument drive, as well as a sterile adapter and a surgical instrument, are connected by engaging member. For example, engagement of two engaging members as shown in FIG. 1 is realized by a relative rotation between the two engaging members due to the elasticity of the two engaging members, and the dashed line in FIG. 1 schematically shows a movement path of an engaging member.

However, a gap between the joint surfaces of the engaging members is likely to result in uneven force, unstable engagement, vibration, or the like, which adversely affect stability of the system. Moreover, the existing engagement of the engaging members is also prone to tipping of the surgical instrument.

SUMMARY

A first aspect of embodiments of the present disclosure provides a structure for connecting an instrument drive to a sterile adapter. The instrument drive has a surface on which a plurality of drive fixed engaging members are provided, and the sterile adapter is connected to the instrument drive. The sterile adapter includes: an adapter body, and an adapter connecting assembly provided at the adapter body and configured to fix the adapter body to instrument drive. The adapter connecting assembly includes a plurality of moveable engaging members cooperating with the plurality of drive fixed engaging members, each of the plurality of moveable engaging members is moveable between an engagement position where the moveable engaging member is engaged with a respective one of the plurality of drive fixed engaging members and a detachment position where the moveable engaging member is detached from the respective drive fixed engaging member, and each of the plurality of moveable engaging members has a movement path parallel to a matching surface of the instrument drive matching the sterile adapter.

In the structure for connecting an instrument drive to a sterile adapter provided by the first aspect of embodiments of the present disclosure, engagement can be achieved by relative horizontal movement between the plurality of drive fixed engaging members and the plurality of moveable engaging members. In this way, gaps between the engaging members can be prevented, thereby improving the tightness and stability of the engagement.

In some embodiments, two sets of drive fixed engaging members are provided at the instrument drive and are separated by a drive transmission portion. The adapter connecting assembly includes: two moveable components and one or more resilient components. Each moveable component of the two moveable components includes one set of moveable engaging members corresponding to one respective set of drive fixed engaging members, and each moveable component is moveable relative to the adapter body to move the one set of moveable engaging members between the engagement position and the detachment position. The one or more resilient components is connected with the two moveable components to provide the two moveable components with forces for driving each set of moveable engaging members towards the engagement position.

In some embodiments, the two moveable components are arranged to move together or move separately.

In some embodiments, each set of the two sets of drive fixed engaging members includes at least two drive fixed engaging members spaced from each other, and each moveable engaging member of the one set of moveable engaging members of each moveable component is provided at a position corresponding to a position of a respective drive fixed engaging member of the at least two drive fixed engaging members of each set of the two sets of drive fixed engaging members.

In some embodiments, each moveable component includes an engaging portion and a connecting portion. The one set of moveable engaging members is provided at the engaging portion, and the connecting portion is connected to the one or more resilient components. The one or more resilient components are configured to provide the forces for driving each set of moveable engaging members towards the engagement position, and an extension direction of the engaging portion is perpendicular to a direction of the forces provided by the one or more resilient components.

In some embodiments, the engaging portion extends from one side or two opposing sides of the connecting portion, and moveable engaging members of the one set of moveable engaging members are spaced from each other along the extension direction of the engaging portion.

In some embodiments, each moveable component further includes an operation button provided at the engaging portion or the connecting portion.

In some embodiments, each drive fixed engaging member of the two sets of drive fixed engaging members has a top surface configured as an inclined surface or a curved surface, and inclined surfaces or curved surfaces of one set of the two sets of drive fixed engaging members face towards inclined surfaces or curved surfaces of the other set of the two sets of drive fixed engaging members.

In some embodiments, each moveable engaging member of two sets of moveable engaging members has a bottom surface configured as an inclined surface or a curved surface, and inclined surfaces or curved surfaces of one set of the two sets of moveable engaging members face away from inclined surfaces or curved surfaces of the other set of the two sets of moveable engaging members.

In some embodiments, the adapter connecting assembly includes one resilient component, and the two moveable components include a first moveable component and a second moveable component. The first moveable component includes a first engaging portion and a first connecting portion connected to the first engaging portion, and one set of two sets of moveable engaging members is provided at the first engaging portion. The second moveable component includes a second engaging portion and a second connecting portion connected to the second engaging portion, and the other set of the two sets of moveable engaging members is provided at the second engaging portion. The one resilient component is connected to the first connecting portion and the second connecting portion, to enable a relative movement between the first moveable component and the second moveable component.

In some embodiments, the first connecting portion defines a cavity, the second connecting portion includes a protrusion at least partially extends into the cavity. The protrusion is moveable along the cavity.

In some embodiments, the one resilient component is arranged in the cavity, the one resilient component has one end abutting against a side wall defining the cavity, and another end abutting against the protrusion.

In some embodiments, the one resilient component is a spring. The first connecting portion has a first fixing column protruding from a side wall of the cavity towards the second connecting portion, and the second connecting portion has a second fixing column protruding from an end of the protrusion towards the first connecting portion. One end of the spring is sleeved on the first fixing column, and an other end of the spring is sleeved on the second fixing column.

In some embodiments, the adapter body includes a partition board, the adapter connecting assembly includes two resilient components provided at two opposing sides of the partition board, respectively, and the two resilient components are connected to the partition board. Each moveable component of the two moveable components is connected to a respective resilient component of the two resilient components, and the two moveable components are symmetrical about the partition board.

In some embodiments, one drive fixed engaging member of the two sets of drive fixed engaging members includes an extension portion and an abutment portion, the abutment portion has an abutment surface configured as a bottom surface of the abutment portion, and a top surface of the abutment portion forms a top surface of the one drive fixed engaging member. One moveable engaging member of two sets of moveable engaging members defines a groove opening outwards, the one moveable engaging member includes a bottom wall defining the groove and having a fitting surface facing the groove, and the abutment surface abuts on the fitting surface in an engagement of the one drive fixed engaging member with the one moveable engaging member.

A second aspect of embodiments of the present disclosure provides a structure for connecting a sterile adapter to a surgical instrument. The sterile adapter has a top surface on which a plurality of adapter fixed engaging members are provided, and the surgical instrument is connected to the sterile adapter. The surgical instrument includes: a base and at least one instrument fixing assembly provided at the base and configured to fix the base to the sterile adapter. Each of the at least one instrument fixing assembly includes an instrument moveable component provided with a plurality of moveable engaging members cooperating with the plurality of adapter fixed engaging members. The instrument moveable component is moveable between a locked position where the plurality of moveable engaging members are engaged with the plurality of adapter fixed engaging members and an unlocked position where the plurality of moveable engaging members are detached from the plurality of adapter fixed engaging members, and the instrument moveable component has a movement path parallel to a surface of the sterile adapter.

In the structure for connecting a sterile adapter to a surgical instrument provided by the second aspect of embodiments of the present disclosure, engagement can be achieved by relative horizontal movement between the plurality of adapter fixed engaging members and the plurality of moveable engaging members. In this way, gaps between the engaging members can be prevented, thereby improving the tightness and stability of the engagement, and preventing tipping of the surgical instrument.

In some embodiments, two sets of adapter fixed engaging members are provided at the top surface of the sterile adapter, and the two sets of adapter fixed engaging members are provided at two side edges of the sterile adapter opposite to each other, respectively. The surgical instrument includes two instrument fixing assemblies provided at two side edges of the base corresponding to the two side edges of the sterile adapter, respectively, and each instrument fixing assembly of the two instrument fixing assemblies corresponds to a respective set of adapter fixed engaging members. Each instrument moveable component has a set of moveable engaging members arranged along an extension direction of a respective side edge of the two side edges of the sterile adapter.

In some embodiments, each set of the two sets of adapter fixed engaging members includes at least two adapter fixed engaging members spaced from each other, and each instrument moveable component has at least two moveable engaging members spaced from each other.

In some embodiments, each instrument moveable component moves along an arrangement direction of the set of moveable engaging members.

In some embodiments, each instrument fixing assembly of the two instrument fixing assemblies further includes a guide portion and a first resilient component. The guide portion extends along a direction parallel to the two side edges of the base, the instrument moveable component is provided at the guide portion defining a movement path for the instrument moveable component, and the instrument moveable component is movable along the direction parallel to the two side edges of the base. The first resilient component is provided at the guide portion and connected with the instrument moveable component, and a resilient force provided by the first resilient component causes the instrument moveable component to tend to move towards the locked position.

In some embodiments, each instrument fixing assembly of the two instrument fixing assemblies further includes a first connecting seat provided at the base and a second connecting seat provided at the base and separated from the first connecting seat. The guide portion is arranged between the first connecting seat and the second connecting seat, to enable the instrument moveable component to move between the first connecting seat and the second connecting seat.

In some embodiments, the guide portion includes a sliding rod at least partially extending into the instrument moveable component, the sliding rod is connected to one or more of the first connecting seat and the second connecting seat, and the instrument moveable component is moveable along the sliding rod.

In some embodiments, the instrument moveable component includes a moveable component body having a first end close to the first connecting seat and a second end close to the second connecting seat, and the moveable component body defines a channel passing through the moveable component body from the first end to the second end. The sliding rod runs through the channel and is limited by the guide portion.

In some embodiments, the first resilient component is sleeved on the sliding rod and is arranged between the second end of the moveable component body and the second connecting seat, a distance between the first end and the first connecting seat is changeable; or the first resilient component is arranged between the first end of the moveable component body and the first connecting seat, to make the distance between the first end and the first connecting seat changeable.

In some embodiments, the surgical instrument further includes an unlocking assembly including a baffle and an operation button. The baffle is fixedly connected to the base, and at least one through hole is defined in the baffle. The operation button includes: a button body having a side facing towards the baffle, at least one limiting clasp connected to the button body, and an actuating portion formed on a bottom of the button body and protruding downwards the button body. One respective limiting clasp of the at least one limiting clasp includes a body portion and a hook portion formed on an end of the body portion, the body portion extends through a respective through hole of the at least one through hole to enable the operation button to move towards or away from the baffle, and the hook portion is configured to hook on an edge of the respective through hole to prevent the one respective limiting clasp from coming out of the respective through hole. An actuated portion protruding from the moveable component body is formed on the moveable component body. The actuating portion interferes with the actuated portion in response to the button body getting close to the baffle, to enable the moveable component body to move towards the unlocked position, and the actuating portion detaches from the actuated portion in response to the button body getting far away the baffle, to enable the moveable component body to move towards the locked position.

In some embodiments, the actuating portion has an actuating surface, the actuated portion has an actuated surface, the actuating surface and the actuated surface are in sliding fitting, and both the actuating surface and the actuated surface are configured as inclined surfaces; or the actuating portion is configured as a rolling part, the actuated portion has the actuated surface, the rolling part and the actuated surface are in rolling fitting, and the actuated surface is configured as an inclined surface.

In some embodiments, each instrument fixing assembly of the two instrument fixing assemblies further includes a second resilient component arranged between and connected to the button body and the baffle, and a resilient force provided by the second resilient component causes the button body to tend to move away from the baffle.

A third aspect of embodiments of the present disclosure provides a surgical robot, including one or more of the structure for connecting an instrument drive to a sterile adapter as illustrated in the first aspect and the structure for connecting a sterile adapter to a surgical instrument as illustrated in the second aspect. The surgical robot provided by the present disclosure has technical effects similar to those of the above-mentioned first aspect and/or second aspect.

BRIEF DESCRIPTION OF THE DRAWINGS

In order to illustrate the technical solutions in the embodiments of the present disclosure more clearly, the drawings involved in the embodiments of the present disclosure will be briefly described below. For those of ordinary skill in the art, other drawings may be obtained in accordance with these drawings without any inventive effort.

DETAILED DESCRIPTION OF THE EMBODIMENTS

The features and exemplary embodiments according to aspects of the present disclosure will be illustrated in detail below. In order to make the purposes, technical solutions, and advantages of the present disclosure more apparent, the following will refer to the accompanying drawings and exemplary embodiments to illustrate the present disclosure in further detail. It should be understood that the illustrated embodiments herein are only for the purpose of explaining the present disclosure, rather than limiting the present disclosure. For those skilled in the art, the present disclosure can be implemented without some of the specific details. The illustration of the embodiments below is only intended to provide a better understanding of the present disclosure by showing examples of the present disclosure.

It should be noted that relational terms such as first and second herein are only used to distinguish one entity or operation from another entity or operation, and do not necessarily require or imply any actual relationship or order between these entities or operations. The terms "comprising", "including", or any other variation thereof are intended to encompass non-exclusive inclusion, such that a process, method, item, or device that includes a series of elements not only includes those elements, but also other elements that are not explicitly listed, or further includes elements inherent in such a process, method, item, or device. Without further limitations, the elements limited by the statement "including . . . " do not exclude the existence of other identical elements in the process, method, item, or device that includes the elements.

Exemplary embodiments of the present disclosure will be illustrated in detail referring to FIGS. 2 to 13.

Figure 1:
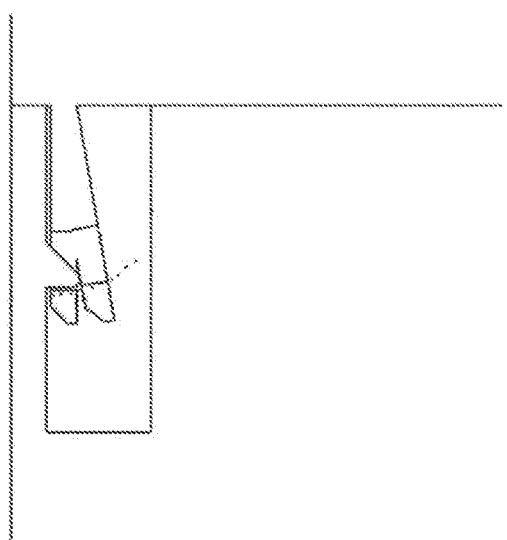
FIG. 1 is a schematic diagram of a moving status of an engaging member during engagement of a conventional instrument drive with a conventional sterile adapter in some situations.
Figure 2:
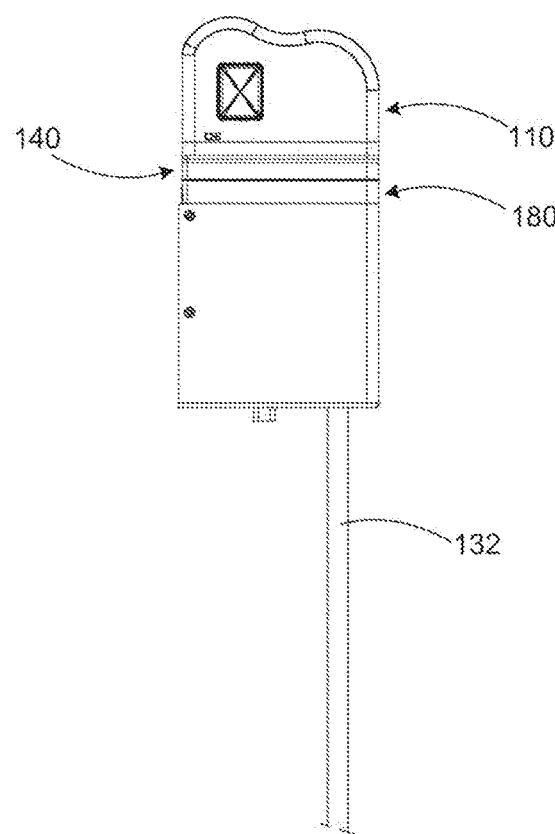
FIG. 2 is a structural schematic diagram of the instrument driving part of the surgical robot according to some embodiments of the present disclosure.
Figure 3:
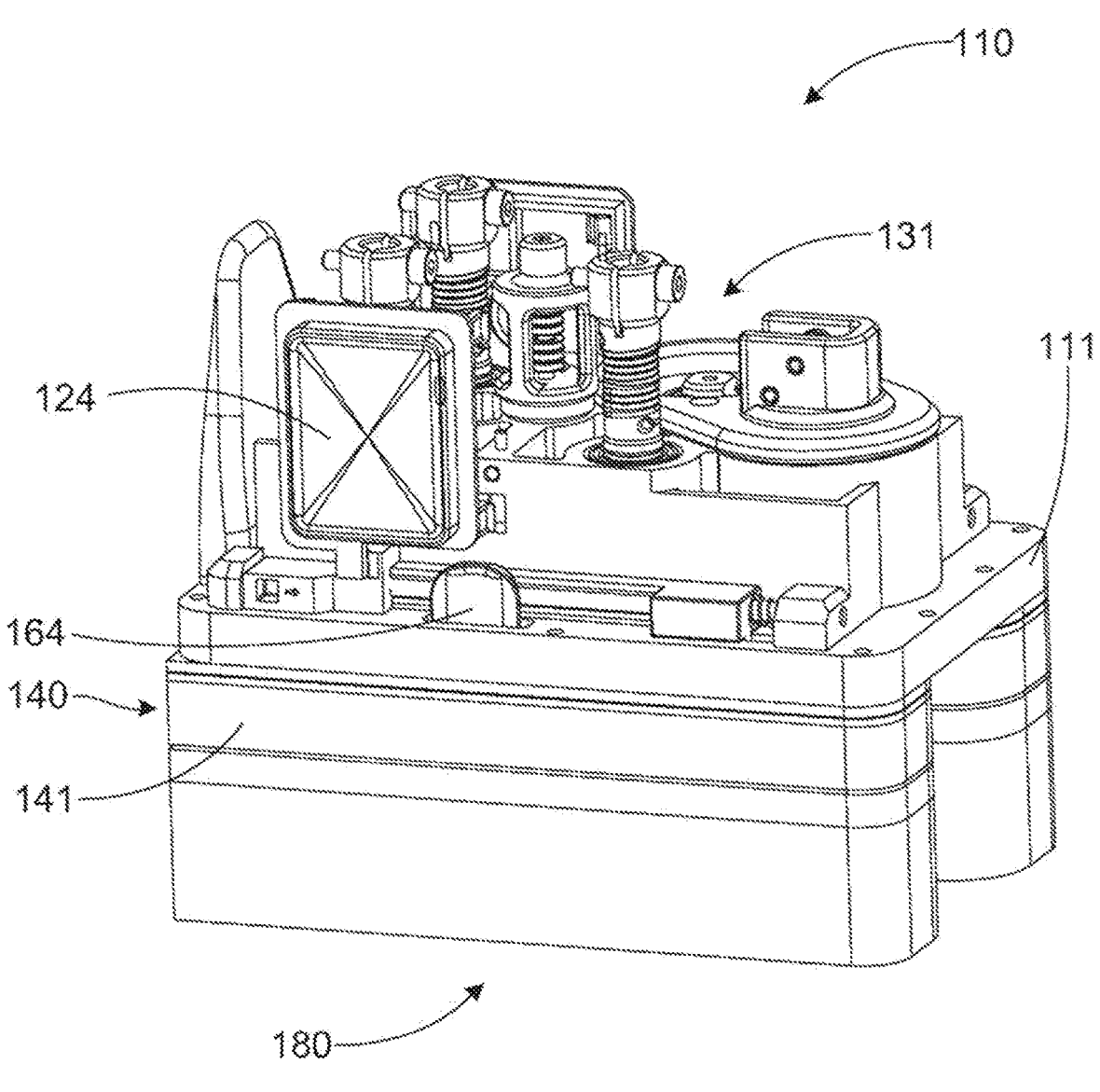
FIG. 3 is a schematic diagram of the mounting structure of a back end of the instrument of the surgical robot in FIG. 2.
Figure 4:
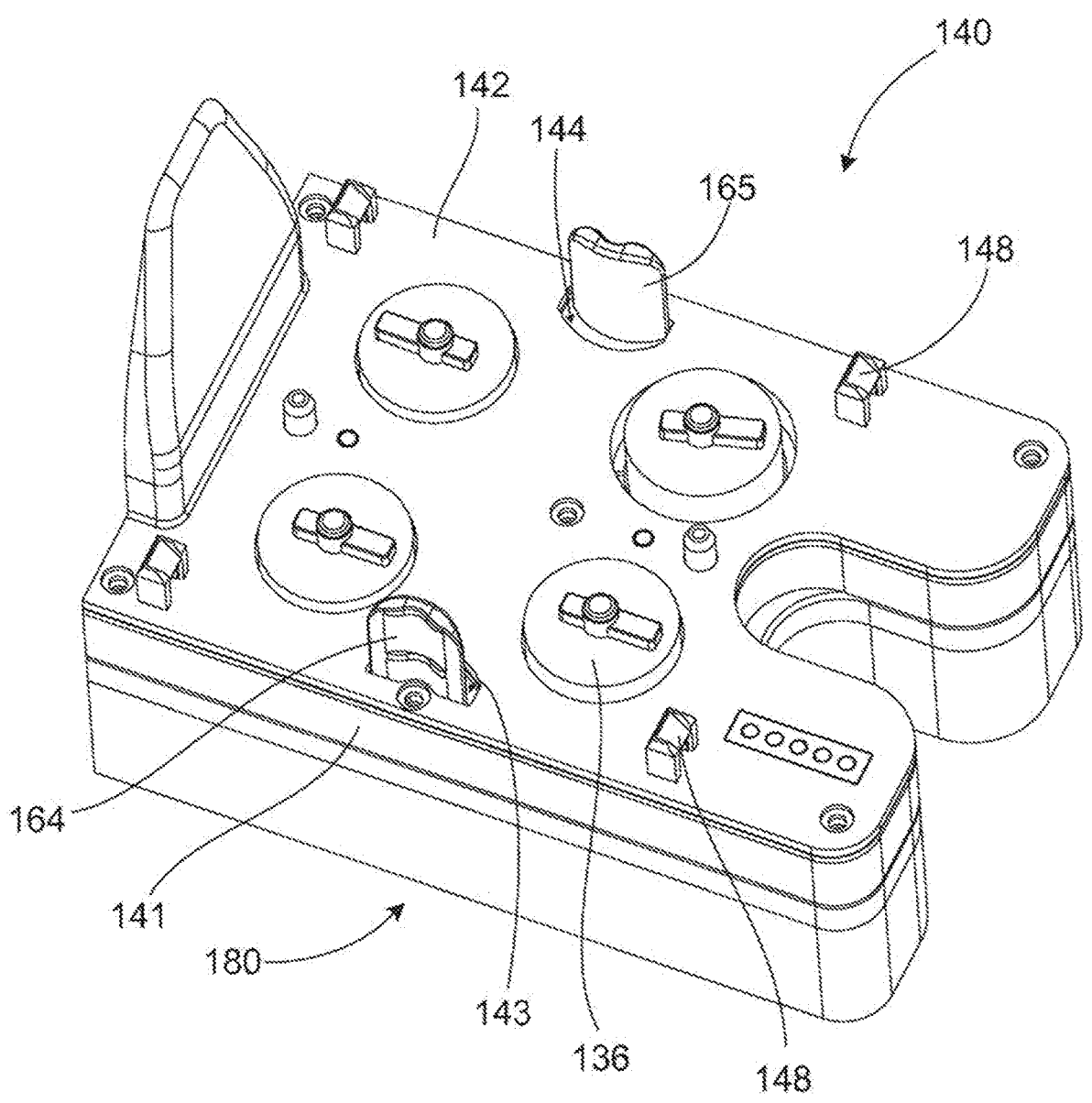
FIG. 4 is a schematic diagram of the structure for connecting the instrument drive to the sterile adapter of the surgical robot in FIG. 3.
Figure 13:
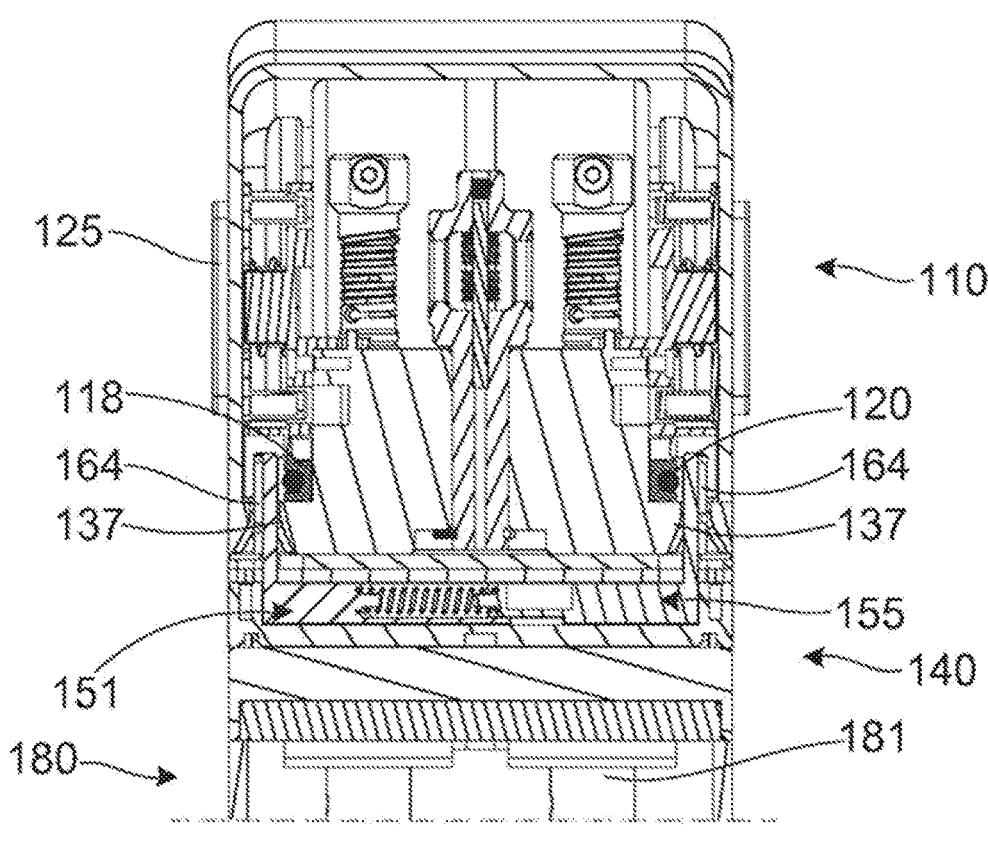
FIG. 13 is a sectional schematic diagram of the surgical robot in FIG. 2.

Referring to FIGS. 2, 3 and 13, a surgical robot 100 according to the present disclosure may include a surgical instrument 110, a sterile adapter 140 and an instrument drive 180. The sterile adapter 140 is connected to the instrument drive 180, and the surgical instrument 110 is connected to the sterile adapter 140. In some embodiments, a bottom surface of the sterile adapter 140 is fitted and connected to a top surface of the instrument drive 180.

A front end of the surgical instrument 110 is configured as surgical tools such as pliers, scissors, clip lights, or the like, and a back end of the surgical instrument 110 is connected to a top surface of the sterile adapter 140. The instrument drive 180 provides driving forces to an instrument actuator 131 at back end of the surgical instrument 110 through the sterile adapter 140, such that the aforementioned surgical tools can perform pitching, yawing, and gripping through a traction assembly (such as wire ropes or the like) in the sleeve 132. Both of a structure for connecting the instrument drive 180 to the sterile adapter 140 and a structure for connecting the sterile adapter 140 to the surgical instrument 110 are implemented by engaging member connection.

Figure 5:
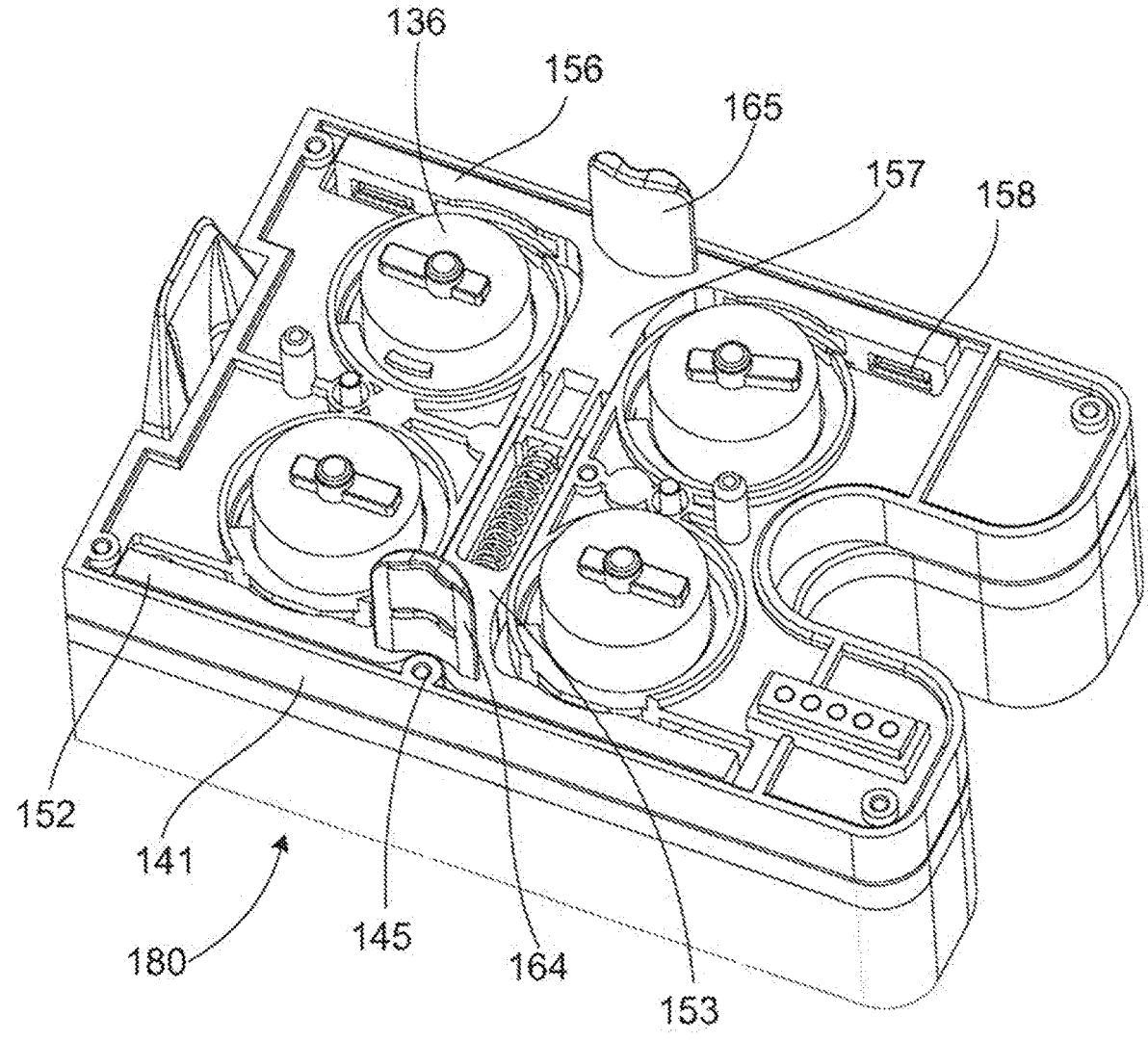
FIG. 5 is a schematic diagram of the structure for connecting the instrument drive to the sterile adapter in FIG. 4, with an adapter cover being omitted.
Figure 6:
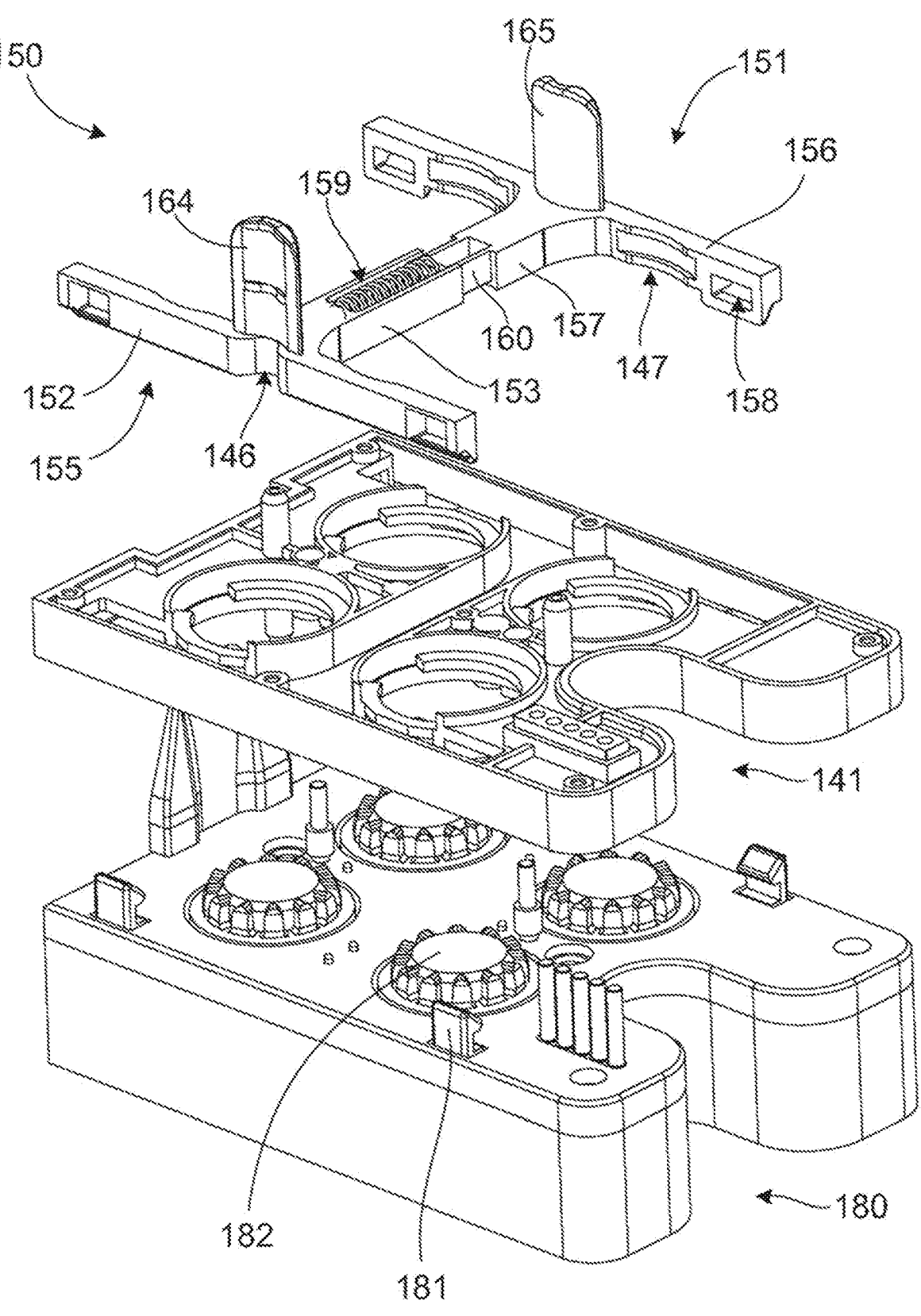
FIG. 6 is an exploded schematic diagram of the structure for connecting the instrument drive to the sterile adapter in FIG. 5.

The structure for connecting the instrument drive 180 to the sterile adapter 140 is shown in FIGS. 4, 5, 6 and 7. The instrument drive 180 has a surface on which a plurality of drive fixed engaging members 181 are provided (as shown in FIG. 6). There may be one or more sets of drive fixed engaging members. In some embodiments, a set of drive fixed engaging members refers to two drive fixed engaging members. It should be understood that a set of drive fixed engaging members may also refer to 3, 4, 5, 6 drive fixed engaging members or the like.

The sterile adapter 140 includes an adapter body 141, an adapter cover 142 and an adapter connecting assembly 150. A bottom of the adapter body 141 is connected to a top surface of the instrument drive 180, so that the plurality of drive fixed engaging members 181 at least partially extend into the adapter body 141. The adapter cover 142 is fixedly connected to the adapter body 141.

The adapter connecting assembly 150 is at least partially arranged in the adapter body 141. The adapter connecting assembly 150 includes a plurality of moveable engaging members cooperating with the plurality of drive fixed engaging members 181, such that the adapter connecting assembly 150 can fix the adapter body 141 to the instrument drive 180. Each moveable engaging member of the plurality of moveable engaging members is moveable between an engagement position where the moveable engaging member is engaged with a respective one of the plurality of drive fixed engaging members 181 and a detachment position where the moveable engaging member is detached from the respective drive fixed engaging member 181, and each of the plurality of moveable engaging members has a movement path parallel to a matching surface of the instrument drive 180 matching the sterile adapter 140.

In some embodiments, each drive fixed engaging member 181 has a top surface configured as an inclined surface or a curved surface, each moveable engaging member also has a bottom surface configured as an inclined surface or a curved surface, and the top surface of each drive fixed engaging member 181 is configured to be able to cooperate with the bottom surface of each moveable engaging member. In this way, during assembly, when the adapter connecting assembly moves downwards, the bottom surface of each moveable engaging member presses on the top surface of a respective drive fixed engaging member 181, such that each moveable engaging member moves transversely and inwards under the action of pressing. As the adapter connecting assembly 150 continues to move downwards, pressing interference between the bottom surface of each moveable engaging member and the top surface of the respective drive fixed engaging member 181 ends, and the moveable engaging member rebounds under the action of the resilient component 161 (will be described in detail below), thereby implementing the engagement.

In some embodiments, one drive fixed engaging member 181 includes an extension portion and an abutment portion, and the abutment portion has an abutment surface configured as a bottom surface of the abutment portion. One moveable engaging member includes a bottom wall defining a groove and having a fitting surface facing upwards. When the one moveable engaging member engages with the one drive fixed engaging member 181 by relative horizontal movement, the abutment surface abuts on the fitting surface. In this way, engagement without any gap can be achieved by contact fitting between surfaces.

In the surgical robot provided by the embodiments of the present disclosure, engagement can be achieved by relative horizontal movement between the plurality of drive fixed engaging members 181 and the plurality of moveable engaging members. In this way, gaps between the engaging members can be prevented, thereby improving the tightness and stability of the engagement.

In some embodiments, two sets of drive fixed engaging members 181 are provided at the instrument drive 180, and these two sets of drive fixed engaging members 181 are arranged to separate from and be opposite to each other. In some embodiments, the two sets of drive fixed engaging members 181 are formed near two side edges of the instrument drive 180 opposite to each other, respectively, and drive fixed engaging members of each set of the two sets of drive fixed engaging members 181 are spaced from each other and are arranged at a respective side edge. The abutment portions of one set of drive fixed engaging members 181 face towards the abutment portions of the other set of drive fixed engaging members 181.

Accordingly, two sets of moveable engaging members are provided at the adapter connecting assembly 150, and positions and numbers of the two sets of moveable engaging members correspond to those of the above-mentioned drive fixed engaging members 181. In other words, the plurality of moveable engaging members and the plurality of drive fixed engaging members 181 have the same arrangement. The two sets of moveable engaging members may move together or move separately. To this end, the adapter connecting assembly 150 may include two moveable components.

Each moveable component includes one set of moveable engaging members, and each moveable component may be moveable relative to the adapter body 141 to move the one set of moveable engaging members between the engagement position and the detachment position. In some embodiments, each moveable component may be configured to have a roughly "T" shape, and the one set of moveable engaging members may be provided at intervals at the head (i.e., a transverse portion) of the "T" shape. A tail (i.e., a vertical portion) of the "T" shape of one moveable component faces towards that of the "T" shape of the other moveable component. In this way, a plurality of drive fixed engaging members 181 can be arranged on the instrument drive 180 and spaced from each other (or arranged in a scattered manner). Accordingly, a plurality of moveable engaging members also may be spaced from each other (or arranged in a scattered manner). The two moveable component may move separately or move together by linkage therebetween. With the above configuration, multi-points engagement between the instrument drive 180 and the sterile adapter 140 can be achieved by the cooperation of the two sets of moveable engaging members with the two sets of drive fixed engaging members 181. Moreover, linkage can be achieved upon engagement of the one set of moveable engaging members of each moveable component, facilitating detachment. In some embodiments, each moveable engaging member is configured as a groove opening outwards.

In some embodiments, the two moveable components may have a same configuration, and the adapter body 141 may include a partition board (not shown) arranged in the middle of the adapter body 141.

The abovementioned two moveable components are provided at two opposing sides of the partition board and are connected to the partition board, and the two moveable components are symmetrical about the partition board. The adapter connecting assembly 150 includes two resilient components 161. Each moveable component is connected to the partition board via one resilient component 161, and a resilient force provided by the one resilient component 161 causes the set of moveable engaging members to tend to move towards the engagement position.

Figure 7:
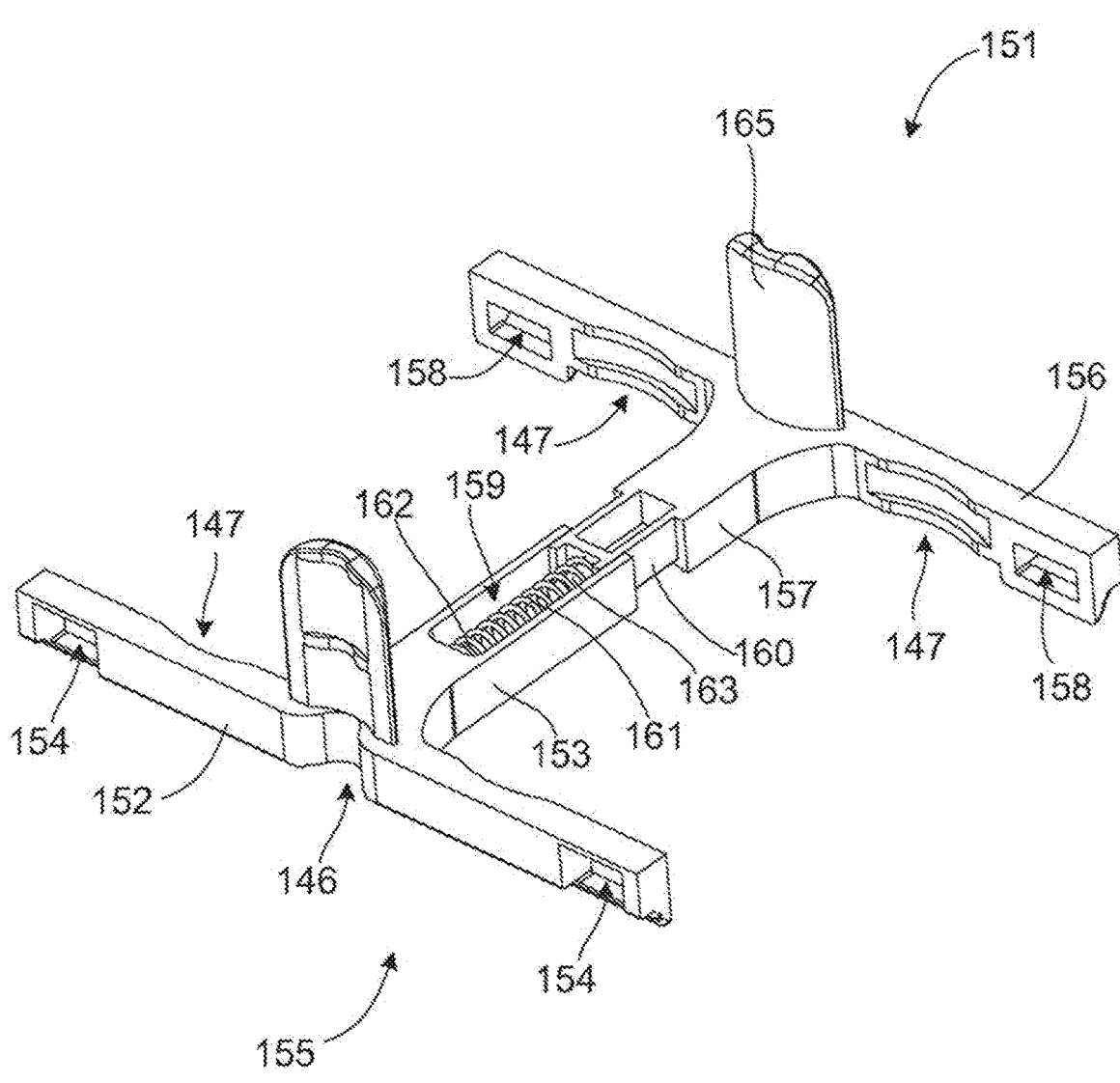
FIG. 7 is a structural schematic diagram of the adapter connecting assembly in FIG. 6.
Figure 8:
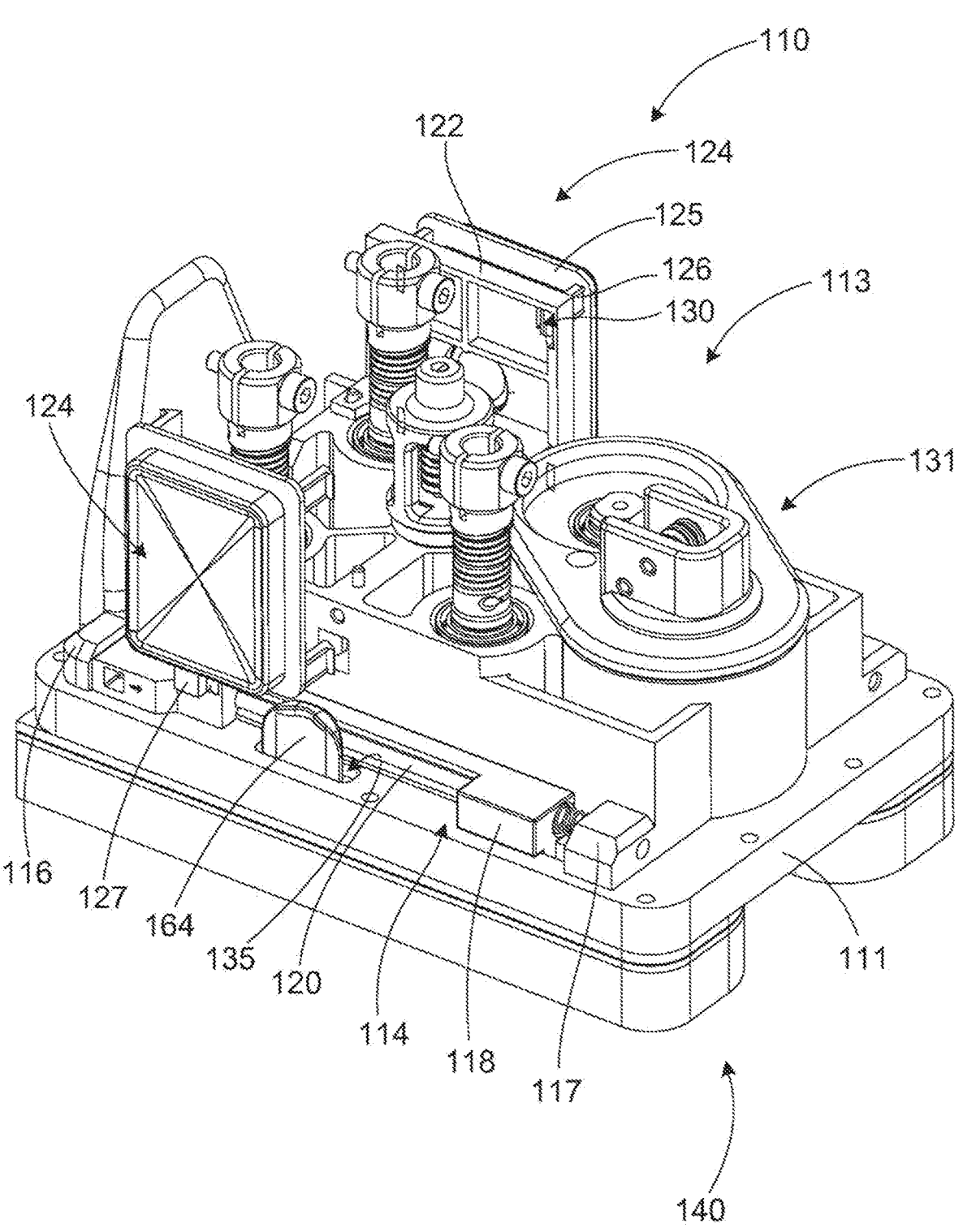
FIG. 8 is a schematic diagram of the structure for connecting the sterile adapter to the back end of the surgical instrument of the surgical robot in FIG. 3.

In the embodiments as shown in FIGS. 5 to 7, the two moveable components include a first moveable component 151 and a second moveable component 155. The first moveable component 151 includes a first engaging portion 152 and a first connecting portion 153 connected to the first engaging portion 152. One set of moveable engaging members, referring to as first moveable engaging members 154, is provided at the first engaging portion 152. The second moveable component 155 includes a second engaging portion 156 and a second connecting portion 157 connected to the second engaging portion 156. One set of moveable engaging members, referring to as second moveable engaging members 158, is provided at the second engaging portion 156.

The first connecting portion 153 and the second connecting portion 157 is connected by one resilient component

161, to enable a relative movement between the first moveable component 151 and the second moveable component 155. Similar to the above-mentioned embodiments that are not shown, the resilient component 161 provides resilient forces to the first moveable component 151 and the second moveable component 155 which cause the plurality of moveable engaging members to tend to move towards the engagement position.

Thus, when the plurality of moveable engaging members are in the engagement position, the first moveable component 151 and/or the second moveable component 155 may move towards each other under pushing of the user (pushing on an operation button, which will be described in detail hereinafter), to move the plurality of moveable engaging members into the detachment position. When the plurality of moveable engaging members are in the detachment position, the first moveable component 151 and/or the second moveable component 155 may move far away from each other under pushing of the resilient component 161, to move the plurality of moveable engaging members into the engagement position. Extension directions of the first engaging portion 152 and the second engaging portion 156 are perpendicular to a direction of the forces provided by the resilient component 161.

The structure of the adapter connecting assembly 150 will be more specifically introduced in conjunction with FIG. 7 below. The first engaging portion 152 extends from the first connecting portion 153 towards two opposing sides, and one set of moveable engaging members are provided at intervals along the extension direction of the first connecting portion 153. The second engaging portion 156 extends from the second connecting portion 157 towards two opposing sides, and the other set of moveable engaging members are provided at intervals along the extension direction of the second connecting portion 157. That is to say, the first engaging portion 152 and the second engaging portion 156 forms heads of the "T" shapes, and the first connecting portion 153 and the second connecting portion 157 forms tails of the "T" shapes.

In some embodiments, each moveable component may be configured to have a roughly "L" shape, i.e. the engaging portion extends from the connecting portion towards one side. Specifically, the first engaging portion 152 extends from the first connecting portion 153 towards one side, the second engaging portion 156 also extends from the second connecting portion 157 towards one side, and the first connecting portion 153 and/or the second connecting portion 157 are arranged to be close to a guide back board (not shown).

A cavity 159 is defined at an end of the first connecting portion 153 away from the first engaging portion 152, and a protrusion 160 is formed at an end of the second connecting portion 157 away from the second engaging portion 156. The protrusion 160 at least partially extends into the cavity 159, such that the protrusion 160 can move back and forth along the cavity 159. A circumferential size of the protrusion 160 is smaller than a circumferential size of the cavity 159, making the first connecting portion 153 and the second connecting portion 157 self-steering.

In some embodiments, the resilient component 161 is a spring arranged in the cavity 159 and abutting between the first connecting portion 153 and the second connecting portion 157. Specifically, the resilient component 161 has one end abutting against a side wall defining the cavity 159, and the other end of the resilient component is connected to the protrusion 160. The protrusion 160 may be configured to have a shape similar to that of the cavity 159, i.e. a square or rectangular shape.

In order to ensure that the resilient component 161 is stably mounted in the cavity 159, a first fixing column 162 protruding towards the second connecting portion 157 is formed on an end of the first connecting portion 153, the first fixing column is formed at a closed end of the cavity 159; and a second fixing column 163 protruding towards the first connecting portion 153 is formed on an end of the second connecting portion 157. One end of the spring is sleeved on the first fixing column 162, and the other end of the spring is sleeved on the second fixing column 163, in order to form stable supports.

In some embodiments not shown, the protrusion 160 may be configured as a cylinder at least partially extending into the spring. Thus, the protrusion also may form a support for the spring.

In some embodiments, each of the first connecting portion 153 and the second connecting portion 157 may have a limiting part for preventing the first connecting portion 153 from detaching from the second connecting portion 157. The limiting parts may be formed at an end of the first connecting portion 153 and an end of the second connecting portion 157 close to each other, respectively, and the two limiting parts may clamp or engage with each other, such that the first moveable component 151 does not easily detach from the second moveable component 155 after assembly.

Referring to FIGS. 4 to 7, the first moveable component 151 further includes a first operation button 164 provided at the first engaging portion 152 or the first connecting portion 153. In some embodiments, the first operation button 164 is provided at a junction of the first connecting portion 153 and the first engaging portion. The second moveable component 155 further includes a second operation button 165 having a structure and a mounting position similar to those of the first operation button 164, which will not be repeated here. The user may push the first operation button 164 and/or the second operation button 165 to unlock.

A first opening 143 and a second opening 144 spaced apart from each other is defined on the adapter cover 142. The positions of the first opening 143 and the second opening 144 correspond to the positions of the first operation button 164 and the second operation button 165, respectively, so that the first operation button 164 and the second operation button 165 can extend through the first opening 143 and the second opening 144, respectively, to protrude from a top surface of the adapter cover 142. Moreover, the cross-sectional dimensions of the first opening 143 and the second opening 144 are larger than those of the first operation button 164 and the second operation button 165, respectively, to reserve the moving space for the first operation button 164 and the second operation button 165.

In some embodiments, the two operation buttons may be provided at two side surfaces of the sterile adapter 140, respectively, i.e. may be provided at two side portions of the adapter body 141. For example, a hole may be defined on a side portion of the adapter body 141, and a respective operation button transversely extends out of the hole to prevent the case in which the respective operation button protrudes upwards and interferes with other components.

One or more screw receiving portions 145 are formed on the adapter body 141, and the adapter cover 142 may be connected to the adapter body 141 using screws. The one or more screw receiving portions 145 are formed near the first operation button 164 and the second operation button 165. In order to avoid the screw receiving portions 145, recesses

146 that are recessed away from the screw receiving portions 145 are formed at the connection between the first connecting portion 153 and the first engaging portion 152, and at the connection between the second connecting portion 157 and the second engaging portion 156, respectively.

The instrument drive 180 includes a plurality of drive connecting parts 182 forming a drive transmission portion, the sterile adapter 140 further includes a plurality of adapter connecting parts 136, and each adapter connecting part 136 is configured to cooperate with a respective drive connecting part 182. In other words, each adapter connecting part 136 is sleeved on a respective drive connecting part 182. A plurality of recesses 147 that are recessed away from the plurality of drive connecting parts 182 are formed on lateral surfaces of the first engaging portion 152 and the second engaging portion 156 facing towards the plurality of drive connecting parts 182, and a shape of each recess 147 is similar to a shape of a contour of a respective drive connecting part 182, in order to avoid the respective drive connecting part 182.

Moreover, mounting surfaces of the plurality of drive connecting parts 182 may form limits with the above-mentioned plurality of recesses 147. The plurality of drive connecting parts 182 can cooperate with an outer frame of the adapter body 141 to jointly limit the adapter connecting assembly 150 within the adapter body 141.

Referring to FIGS. 8, 9, 10, 11, 12 and 13, in which a structure for connecting the sterile adapter 140 to the surgical instrument 110 is shown. The surgical instrument 110 includes a base 111 connected to the sterile adapter 140, and the base 111 may be attached to the top surface of the adapter cover 142. A first hole 135 and a second hole (not shown) are defined at positions corresponding to the first operation button 164 and the second operation button 165 on the base 111, and the first operation button 164 and the second operation button 165 on the adapter connecting assembly 150 extend through the first hole 135 and the second hole, respectively, thereby protruding from a top surface of the base 111. In this way, smooth installation between surgical instrument 110 and the sterile adapter 140 can be achieved.

Limiting blocks 137 are provided at edges of the first hole 135 and the second hole close to each other, respectively. The two limiting blocks 137 are arranged to be close to the first hole 135 and the second hole, respectively, in order to limit the movements of the first operation button 164 and the second operation button 165 when the surgical instrument 110 is connected to the sterile adapter 140. In some embodiments, the two limiting blocks 137 may be edges of the first hole 135 and the second hole close to the first operation button 164 and the second operation button 165, respectively.

The sterile adapter 140 has a top surface on which a plurality of adapter fixed engaging members 148 are provided. There may be one or more sets of adapter fixed engaging members, and each set of adapter fixed engaging members 148 includes at least two adapter fixed engaging members 148 spaced from each other. In some embodiments, the plurality of adapter fixed engaging members 148 are provided at the surface of the adapter cover 142 and at least partially extend into the base 111.

The surgical instrument 110 includes the above-mentioned instrument actuator 131 and at least one instrument fixing assembly 113. The instrument actuator 131 is provided at the base 111, and the at least one instrument fixing assembly 113 is also provided at the base 111 and is provided at a side of the instrument actuator 131. In some embodiments, the surgical instrument 110 includes two instrument fixing assemblies 113 provided at two opposing sides of the instrument actuator 131 and corresponding to the plurality of adapter fixed engaging members 148 provided at the two opposing sides of the instrument actuator. The two instrument fixing assemblies 113 are configured to fix the base 111 to the sterile adapter 140.

Each instrument fixing assembly 113 includes an instrument moveable component 114 provided with a set of moveable engaging members 115 corresponding to the plurality of adapter fixed engaging members 148, and the set of moveable engaging members 115 includes two or more moveable engaging members 115 spaced from each other. The set of moveable engaging members 115 also extend at least partially into the base 111 to cooperate with the plurality of adapter fixed engaging members 148. In this way, the multi-points engagement is conducive to preventing the occurrence of tipping.

The instrument moveable component 114 is moveable between a locked position where the plurality of moveable engaging members 115 are engaged with the plurality of adapter fixed engaging members 148 and an unlocked position where the plurality of moveable engaging members 115 are detached from the plurality of adapter fixed engaging members 148, and the instrument moveable component 114 has a movement path parallel to a surface of the sterile adapter. In other words, each instrument moveable component 114 can move along the arrangement direction of the set of moveable engaging members 115.

In some embodiments, through holes 112 are defined in the base 111, and each moveable engaging member 115 and the respective adapter fixed engaging member 148 both extend at least partially into a respective through hole of the through holes 112, in order to engage with or detach from each other, thereby fixing the base 111 to the sterile adapter 140.

In some shown embodiments, the through holes 112 are configured as T-shaped grooves. Each adapter fixed engaging member 148 extends from the adapter cover 142 into a head of a respective T-shaped groove, and each moveable engaging member 115 extends from the instrument moveable component 114 into a tail of the respective T-shaped groove and is moveable in the tail.

In some embodiments, each moveable engaging member 115 includes an extension portion and an abutment portion, and the abutment portion has an abutment surface configured as a top surface of the abutment portion. When there are more than one set of moveable engaging members 115, the abutment portions of a same set of moveable engaging members 115 have the same orientation. Each adapter fixed engaging member 148 defines a groove having a fitting surface facing downwards. When there are more than one set of adapter fixed engaging members 148, the openings of a same set of adapter fixed engaging members 148 have the same orientation. When a moveable engaging member 115 engages with a respective adapter fixed engaging member 148 by relative horizontal movement, the abutment portion extends into the groove, and the abutment surface abuts on the fitting surface. In this way, contact fitting between surfaces can be achieved, and a more stable engagement can be obtained.

In the surgical robot 100 provided by the embodiments of the present disclosure, engagement can be achieved by relative horizontal movement between the plurality of adapter fixed engaging members 148 and the plurality of moveable engaging members 115. In this way, gaps between the engaging members can be prevented or reduced, thereby improving the tightness and stability of the engagement.

In some embodiments, two sets of adapter fixed engaging members 148 are provided at the top surface of the adapter cover 142, the two sets of adapter fixed engaging members 148 space apart from each other, and each set of adapter fixed engaging members 148 has a same orientation. Specifically, the two sets of adapter fixed engaging members 148 are provided at two side edges of the sterile adapter 140 opposite to each other, respectively.

Accordingly, the surgical instrument 110 may include two instrument fixing assemblies 113 provided at two side edges of the base 111 corresponding to the two side edges of the sterile adapter 140, respectively. That is to say, the two instrument fixing assemblies are provided at two side edges of the above-mentioned instrument actuator 131, in other words, at the two side edges of the base 111.

Each instrument fixing assembly 113 corresponds to a respective set of adapter fixed engaging members 148. In other words, each instrument moveable component 114 has a set of moveable engaging members 115 arranged along a length direction of the instrument moveable component 114. In this way, the set of moveable engaging members 115 can move together with the instrument moveable component 114, thereby achieving linkage and facilitating engagement and detachment.

Each instrument fixing assembly 113 further includes a guide portion and a first resilient component 121. The guide portions are provided at two side edges of the instrument actuator 131 and extend along a direction parallel to the side edges of the base 111. The instrument moveable component 114 is provided at the guide portion defining a movement path for the instrument moveable component, and the instrument moveable component 114 is movable along the direction parallel to the side edges of the base.

The first resilient component 121 may be provided at the guide portion and connected with the instrument moveable component 114, in order to provide a resilient force to the instrument moveable component 114. The resilient force provided by the first resilient component 121 causes the instrument moveable component 114 to tend to move towards the locked position.

In some embodiments, the moving direction of the instrument moveable component 114 may be parallel to the moving directions of the first moveable component 151 and the second moveable component 155, or the moving direction of the instrument moveable component 114 may be perpendicular to the moving direction of the first moveable component 151 and the second moveable component 155.

In some embodiments, the guide portion may be a sliding groove formed in the base 111 (not shown) or a guide rail protruding from the base 111 (not shown). In some shown embodiments, the guide portion may be configured as a sliding rod 120. The sliding rod 120 may be configured as an integral-type sliding rod or a split-type sliding rod.

Figure 9:
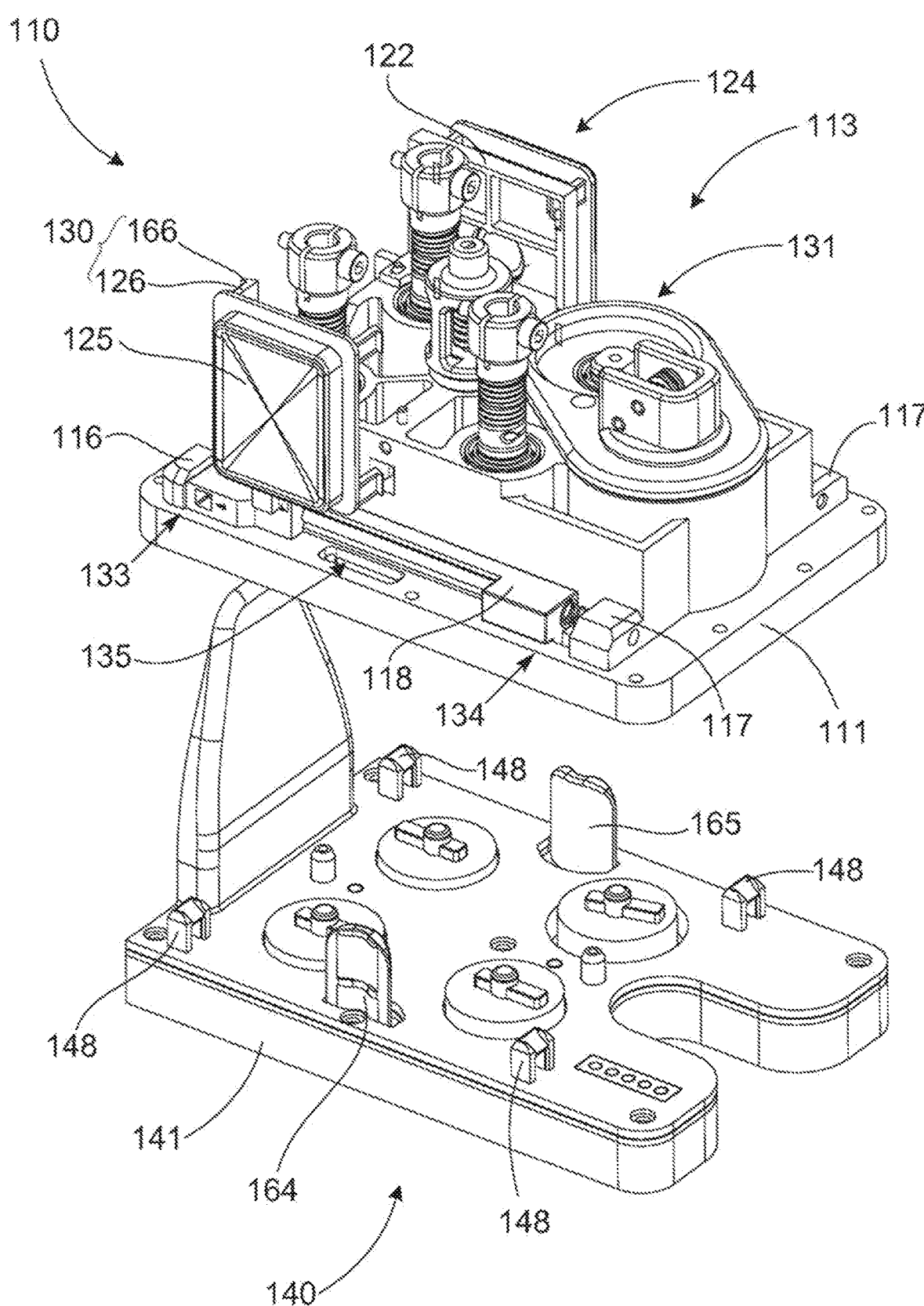
FIG. 9 is an exploded schematic diagram of the structure for connecting the sterile adapter to the back end of the surgical instrument in FIG. 8.
Figure 10:
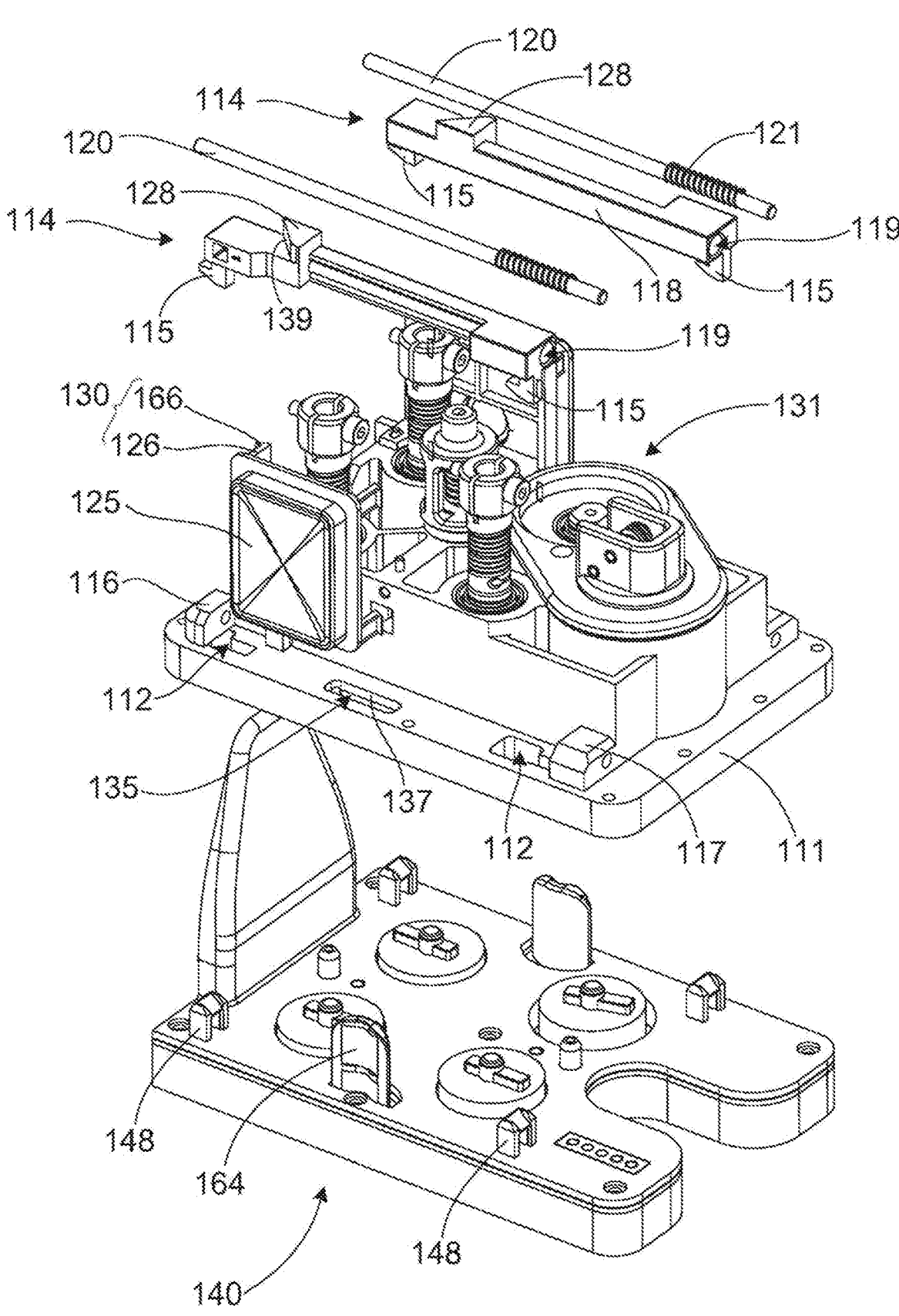
FIG. 10 is an exploded schematic diagram in further detail of the structure for connecting the sterile adapter to the surgical instrument in FIG. 9.
Figure 11:
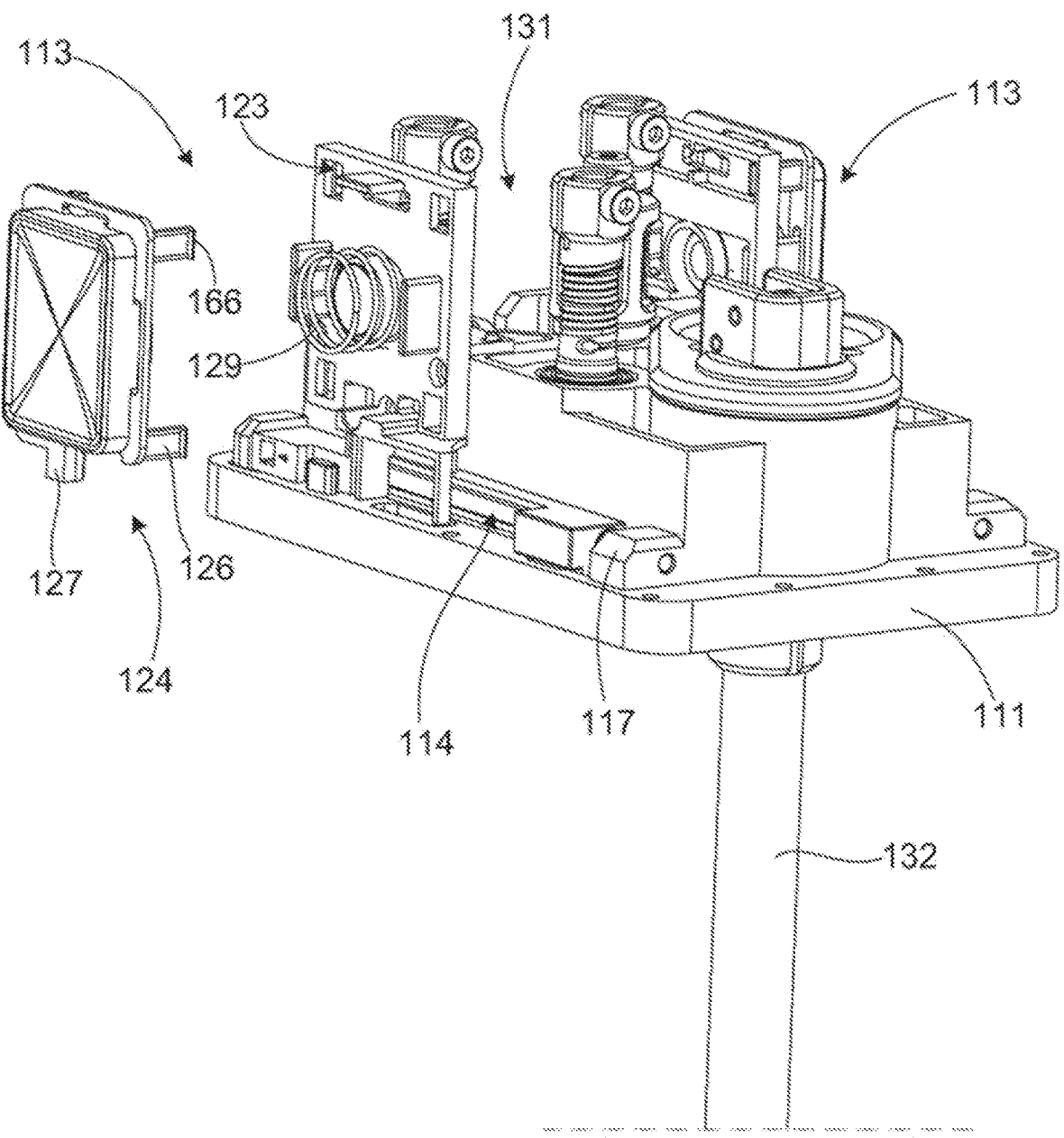
FIG. 11 is a schematic diagram of local structure of the surgical instrument in FIG. 8.
Figure 12:
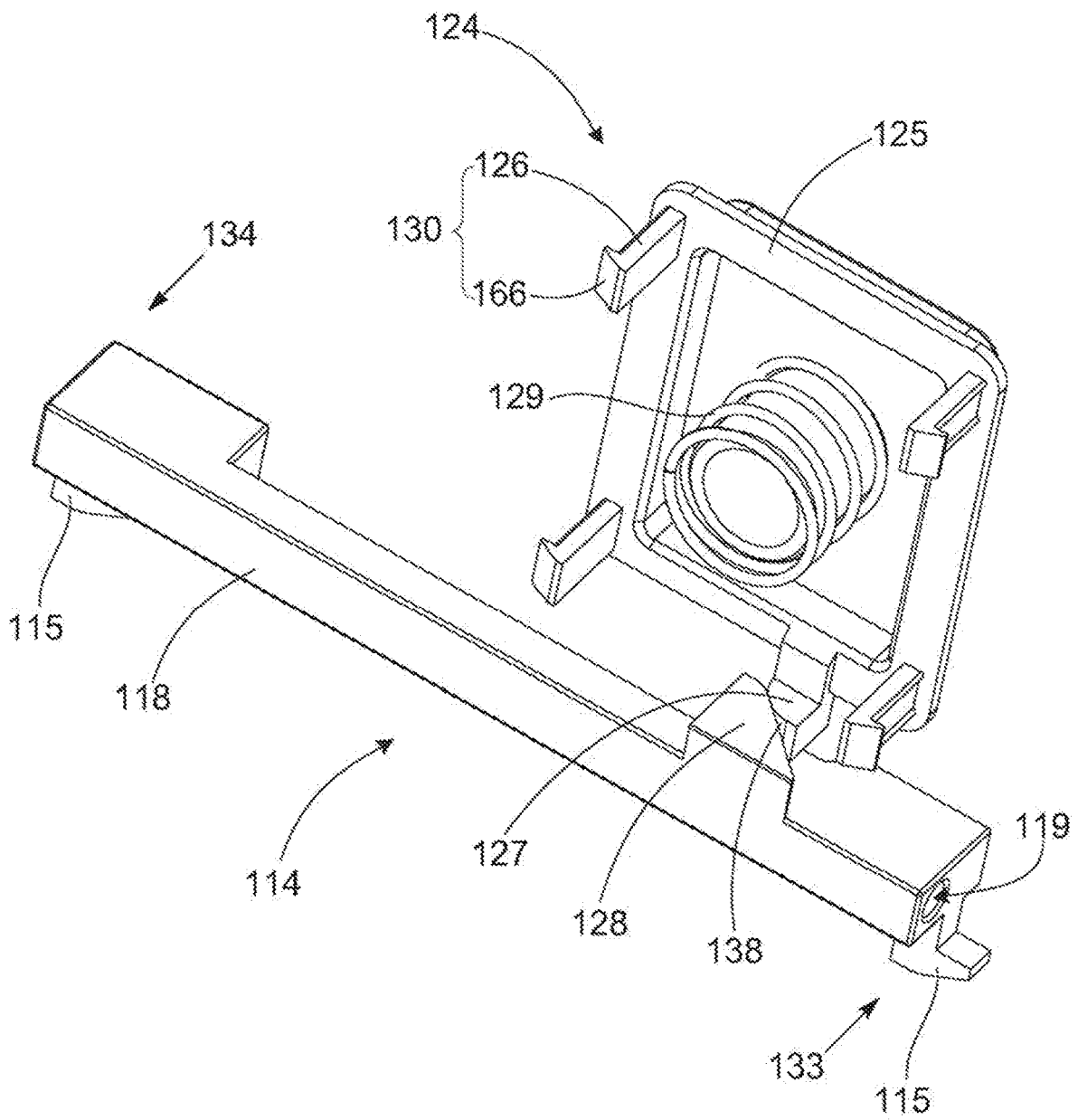
FIG. 12 is a structural schematic diagram of the operation button and the instrument moveable component in FIG. 10.

Referring to FIGS. 9 and 10, each instrument fixing assembly 113 further includes a first connecting seat 116 and a second connecting seat 117. The first connecting seat and the second connecting seat are both provided at the base 111 and are separated from each other. Specifically, the first connecting seat 116 and the second connecting seat 117 are both provided at a side of the instrument actuator 131 and at a side edge of the base 111. Each instrument moveable component 114 includes a moveable component body 118 having a first end 133 close to the first connecting seat 116 and a second end 134 close to the second connecting seat 117.

The guide portion may be arranged between the first connecting seat 116 and the second connecting seat 117, to enable the instrument moveable component 114 to move between the first connecting seat 116 and the second connecting seat 117.

In some embodiments, the guide portion includes a sliding rod 120 connected between the first connecting portion 153 and the second connecting portion 157, in other words, the sliding rod 120 is limited by the guide portion. The sliding rod 120 may extend through the whole moveable component body 118 by running through a channel 119 passing through the moveable component body 118 from the first end 133 to the second end 134 of the moveable component body 118, thereby limiting the movement of the moveable component body 118.

The moveable component body 118 may defines the channel 119 except for both ends, or may be partially or completely exposed from the moveable component body.

In some embodiments, channels 119 are defined at the first end 133 and the second end 134 of the moveable component body, respectively, and the two channels 119 do not communicate with each other. In this case, the sliding rod 120 is configured as a split-type sliding rod extending into the two channels 119, respectively.

Referring to FIGS. 9 and 10, the first resilient component 121 is sleeved on the sliding rod 120 and is arranged between the second end 134 of the moveable component body 118 and the second connecting seat 117, a distance between the first end 133 and the first connecting seat 116 is changeable.

It is easily understandable that the first resilient component 121 may be arranged between the first end 133 of the moveable component body 118 and the first connecting seat 116, to make the distance between the first end 133 and the first connecting seat 116 changeable.

Thus, when the plurality of moveable engaging members 115 are in the locked position, the user may push the instrument moveable component 114 using the operation button 124 (which will be described in detail hereinafter), in order to move the instrument moveable component along a direction of getting close to the second connecting seat 117 and to move the plurality of moveable engaging members 115 into the unlocked position.

When the plurality of moveable engaging members 115 are in the unlocked position, the instrument moveable component 114 may move along a direction of getting far away from the second connecting seat 117 under driving of the first resilient component 121, in order to move the plurality of moveable engaging members 115 into the locked position.

Referring to FIGS. 9, 10, 11 and 12, the surgical instrument 110 further includes an unlocking assembly including a baffle 122 and an operation button 124. The baffle 122 is fixedly connected to the base 111, and at least one through hole 123 is defined in the baffle 122.

The operation button 124 is connected to the baffle and can perform reciprocating movement relative to the baffle 122. The operation button 124 includes a button body 125 and at least one limiting clasp 130 connected to the button body 125. A side of the button body 125 on which the at least one limiting clasp 130 is arranged faces towards the baffle 122. Each limiting clasp 130 extends through a respective through hole of the at least one through hole 112 to enable the operation button 124 to perform reciprocating movement and move towards or away from the baffle 122. The reciprocating movement may be achieved by a second resilient component 129 connected between the button body 125 and the baffle 122. The second resilient component 129 applies a resilient force to the button body 125 to causes the button body 125 to tend to move away from the baffle 122.

Each limiting clasp 130 includes a body portion 126 connected to the button body 125 and a hook portion 166 formed on an end of the body portion 126 far away from the button body 125. The body portion 126 extends through a respective through hole of the at least one through hole 123 and plays a role of guide track. The hook portion 166 is configured to hook on an edge of the respective through hole 123 to prevent the limiting clasp 130 from coming out of the respective through hole 123, thereby keeping the button body 125 on a side of the baffle 122.

The operation button 124 may have four limiting clasps 130 distributed at four corners of the button body 125, respectively. Accordingly, four through holes 123 are defined in the baffle 122.

In order to achieve the locking and unlocking control on the instrument moveable component 114 by the operation button 124, the operation button 124 further includes an actuating portion 127. Accordingly, the instrument moveable component 114 has an actuated portion 128. When the button body 125 gets close to the baffle 122, the actuating portion 127 interferes with the actuated portion 128 to enable the moveable component body 118 to move towards the unlocked position, and when the button body 125 gets far away the baffle 122, the actuating portion 127 detaches from the actuated portion 128, to enable the moveable component body 118 to move towards the locked position.

The actuating portion 127 is formed on a bottom of the button body 125 and protrudes downwards the button body 125. The actuated portion 128 protrudes from the moveable component body 118. The actuating portion 127 has an actuating surface 138, the actuated portion 128 has an actuated surface 139, both the actuating surface and the actuated surface may be configured as inclined surfaces, such that the actuating surface 138 and the actuated surface 139 are in sliding fitting.

In some embodiments, the actuating portion 127 may be configured as a rolling part, such as a bearing or a roller, the actuated portion 128 may have the actuated surface 139 configured as an inclined surface, such that the rolling part and the actuated surface 139 are in rolling fitting.

Thus, when the user presses on the operation button 124, the button body 125 gets close to the baffle 122, and the actuating surface 138 of the actuating portion 127 interferes with the actuated surface 139 of the actuated portion 128. With the cooperation of the actuating portion and the actuated portion, a longitudinal movement of the operation button 124 is converted into a transverse movement of the instrument moveable component 114, such that the instrument moveable component 114 moves towards the unlocked position. When the user releases the operation button 124, the button body 125 gets away from the baffle 122 under the action of the second resilient component 129, and the actuating surface 138 does not interfere with the actuated surface 128 any longer, such that the instrument moveable component 114 moves towards the locked position under the action of the first resilient component 121.

The embodiments of the present disclosure as illustrated hereinbefore do not fully describe all details, nor do they limit the present disclosure to only the illustrated embodiments. Obviously, based on the above description, many modifications and changes may be made. The present disclosure selects and specifically describes these embodiments in order to better explain the principles and practical applications of the present disclosure, so that those skilled in the art can make good use of the present disclosure and modi-
fications based on the present disclosure. The present dis-
closure is only limited by the claims and their full scopes and
equivalents thereof.

What is claimed is:
1. A surgical instrument, applicable to a surgical robot and
configured to engage with an instrument drive through a
sterile adapter, the sterile adapter having a top surface and a
plurality of first engaging members disposed on the top
surface, the surgical instrument comprising:
    a base having a bottom surface attachable to the top
        surface; and
    at least one fixing assembly movably disposed at the base
        and configured to fix the base to the sterile adapter, each
        of the at least one fixing assembly including a move-
        able component provided with a plurality of second
        engaging members operable to engage with the plural-
        ity of first engaging members, the moveable component
        being operable to move translationally relative to the
        base in a translation direction parallel to the bottom
        surface between a locked position where the plurality
        of second engaging members are engaged with the
        plurality of first engaging members and an unlocked
        position where the plurality of second engaging mem-
        bers are detached disengaged from the plurality of first
        engaging members.
2. The surgical instrument according to claim 1, wherein
two sets of first engaging members are provided on the top
surface of the sterile adapter, and the two sets of first
engaging members are provided at two side edges of the
sterile adapter opposite to each other, respectively;
    wherein the surgical instrument includes two fixing
        assemblies provided at two side edges of the base
        corresponding to the two side edges of the sterile
        adapter, respectively, and each fixing assembly of the
        two fixing assemblies corresponds to a respective set of
        first engaging members; and
    wherein a respective moveable component has a set of
        second engaging members movable together with the
        respective moveable component.
3. The surgical instrument according to claim 2, wherein
each moveable component has at least two second engaging
members arranged and spaced from each other in the trans-
lation direction.
4. The surgical instrument according to claim 2, wherein
each fixing assembly of the two instrument fixing assemblies
further includes:
    a guide portion extending along a direction parallel to the
        two side edges of the base, wherein the moveable
        component is provided on the guide portion defining a
        movement path for the moveable component, and the
        moveable component is movable along the direction
        parallel to the two side edges of the base; and
    a resilient component provided on the guide portion and
        connected with the moveable component, wherein a
        resilient force provided by the resilient component
        causes the moveable component to tend to move
        towards the locked position.
5. The surgical instrument according to claim 4, wherein
each fixing assembly of the two instrument fixing assemblies
further includes:
    a first connecting seat provided on the base; and
    a second connecting seat provided on the base and sepa-
        rated from the first connecting seat;
    wherein the guide portion is arranged between the first
        connecting seat and the second connecting seat, the moveable component is movable between the first
        connecting seat and the second connecting seat.
6. The surgical instrument according to claim 5, wherein
the guide portion includes a sliding rod at least partially
extending into the moveable component, the sliding rod is
connected to one or more of the first connecting seat and the
second connecting seat, and the moveable component is
moveable along the sliding rod.
7. The surgical instrument according to claim 6, wherein
the moveable component includes a moveable component
body having a first end close to the first connecting seat and
a second end close to the second connecting seat, and the
moveable component body defines a channel passing
through the moveable component body from the first end to
the second end; and
    wherein the sliding rod runs through the channel and is
        limited by the guide portion.
8. The surgical instrument according to claim 7, wherein
the resilient component is sleeved on the sliding rod and is
arranged between the second end of the moveable compo-
nent body and the second connecting seat, a distance
between the first end and the first connecting seat is change-
able; or
    the resilient component is arranged between the first end
        of the moveable component body and the first connect-
        ing seat, to make the distance between the first end and
        the first connecting seat changeable.
9. The surgical instrument according to claim 7, wherein
the surgical instrument further includes an unlocking assem-
bly including a baffle and an operation button, the baffle is
fixedly connected to the base, and at least one through hole
is defined in the baffle;
    wherein the operation button includes:
    a button body having a side facing towards the baffle;
    at least one limiting clasp connected to the button body,
        wherein one respective limiting clasp of the at least one
        limiting clasp includes a body portion and a hook
        portion formed on an end of the body portion, the body
        portion extends through a respective through hole of
        the at least one through hole, the operation button is
        moveable towards or away from the baffle, and the
        hook portion is configured to hook on an edge of the
        respective through hole to prevent the one respective
        limiting clasp from coming out of the respective
        through hole; and
    an actuating portion formed on a bottom of the button
        body and protruding downwards the button body;
    wherein an actuated portion protruding from the move-
        able component body is formed on the moveable com-
        ponent body; and
    wherein in response to the button body getting close to the
        baffle, the actuating portion interferes with the actuated
        portion, and the moveable component body is move-
        able towards the unlocked position, and in response to
        the button body getting far away the baffle, the actu-
        ating portion detaches from the actuated portion, and
        the moveable component body is moveable towards the
        locked position.
10. The surgical instrument according to claim 9, wherein
the actuating portion has an actuating surface, the actuated
portion has an actuated surface, the actuating surface and the
actuated surface are in sliding fitting, and both the actuating
surface and the actuated surface are configured as inclined
surfaces; or
    the actuating portion is configured as a rolling part, the
        actuated portion has the actuated surface, the rolling part and the actuated surface are in rolling fitting, and the actuated surface is configured as an inclined surface.

11. The surgical instrument according to claim 1, wherein the plurality of second engaging members are moveable together with the moveable component.

12. The surgical instrument according to claim 1, wherein the at least one fixing assembly includes two moveable components spaced from each other in a first direction, and a respective moveable component of the two moveable components is provided with at least two second engaging members that are movable together with the respective moveable component and are arranged and spaced from one another in a second direction transvers to the first direction.

13. The surgical instrument according to claim 12, wherein the second direction is parallel to the translation direction.

14. The surgical instrument according to claim 1, wherein each of the at least one fixing assembly is disposed close to a side edge of the base, and the translation direction is parallel to an extension direction of the side edge.

15. The surgical instrument according to claim 14, further comprising an instrument actuator configured to receive a driving force from the instrument drive, wherein two fixing assemblies are provided at two opposing side edges of the base, and the instrument actuator is disposed between the two fixing assemblies.

16. The surgical instrument according to claim 14, wherein the operation button includes an actuating portion, the moveable component includes an actuated portion, and interference of the actuating portion and the actuated portion converts a movement of the operation button in the moving direction into a movement of the moveable component in the translation direction.

17. The surgical instrument according to claim 1, wherein the surgical instrument further includes an operation button moveable in a moving direction perpendicular to the translation direction, and the moveable component moves in the translation direction with a movement of the operation button in the moving direction.

18. A surgical robot, comprising:

an instrument drive;

a sterile adapter having a top surface and a plurality of first engaging members disposed on the top surface; and a surgical instrument operable to engage with the instrument drive through the sterile adapter, wherein the surgical instrument includes:

a base having a bottom surface attachable to the top surface; and at least one fixing assembly movably disposed at the base and configured to fix the base to the sterile adapter, each of the at least one fixing assembly including a moveable component, the moveable component being provided with a plurality of second engaging members operable to engage with the plurality of first engaging members, the moveable component being operable to move translationally relative to the base in a translation direction parallel to the bottom surface between a locked position where the plurality of second engaging members are engaged with the plurality of first engaging members and an unlocked position where the plurality of second engaging members are disengaged from the plurality of first engaging members.

19. The surgical instrument according to claim 11, wherein the plurality of second engaging members are arranged and spaced from one another in the translation direction.

20. A surgical instrument, applicable to a surgical robot and configured to engage with an instrument drive through a sterile adapter, the sterile adapter having a top surface and a plurality of first engaging members disposed on the top surface, the surgical instrument comprising:

a base having a bottom surface attachable to the top surface;

an instrument actuator disposed at the base and configured to receive a driving force from the instrument drive; and at least one fixing assembly movably disposed at the base and configured to fix the base to the sterile adapter, each of the at least one fixing assembly including a moveable component provided with a plurality of second engaging members operable to engage with the plurality of first engaging members, the plurality of second engaging members being operable to move translationally relative to the base in a translation direction parallel to the bottom surface between a locked position where the plurality of second engaging members are engaged with the plurality of first engaging members and an unlocked position where the plurality of second engaging members are disengaged from the plurality of first engaging members.

* * * * *